United States Patent [19]

Vadgama et al.

[11] Patent Number: 5,531,878
[45] Date of Patent: Jul. 2, 1996

[54] SENSOR DEVICES

[75] Inventors: Pankaj M. Vadgama, Manchester; Sêamus P. J. Higson, Sheffield, both of United Kingdom

[73] Assignee: The Victoria University of Manchester, Manchester, England

[21] Appl. No.: 343,534

[22] PCT Filed: May 13, 1993

[86] PCT No.: PCT/GB93/00982

§ 371 Date: Feb. 17, 1995

§ 102(e) Date: Feb. 17, 1995

[87] PCT Pub. No.: WO93/24828

PCT Pub. Date: Dec. 9, 1993

[30] Foreign Application Priority Data

May 29, 1994 [GB] United Kingdom .................. 9211402

[51] Int. Cl.⁶ .................................................. G01N 27/26
[52] U.S. Cl. .................. 204/415; 204/403; 205/778; 205/792; 205/793; 435/817; 435/287.1; 435/287.9
[58] Field of Search .................................... 204/403, 415, 204/418; 435/288, 291, 817; 205/778, 792, 793

[56] References Cited

U.S. PATENT DOCUMENTS 3,979,274  9/1976  Newman ............................. 204/195 B
5,376,244 12/1994  Preidel ................................ 204/153.17

FOREIGN PATENT DOCUMENTS 216577   4/1987  European Pat. Off. .
2209836  5/1989  United Kingdom .

OTHER PUBLICATIONS

Thomson et al: "Biocompatibility of Diamond-like Carbon Coating, BIOMATERIALS", vol. 12, Jan. 1991, pp. 37–40.
Higson et al: "Diamond-like Carbon Coated Microporous Polycarbonate as a Composite Barrier for a Glucose Electrode", ANALYTICA CHIMICA ACTA, vol. 271, No. 1, Jan. 1993, pp. 125–133.

*Primary Examiner*—Bruce F. Bell
*Attorney, Agent, or Firm*—Cushman Darby & Cushman

[57] ABSTRACT

Sensor devices comprising enzyme electrodes incorporating a microporous membrane coated with the carbonaceous material known as "diamond-like carbon" (most conveniently deposited by decomposition of a hydrocarbon, induced by radiation or a high electric field). The membrane material is preferably a polycarbonate and its thickness preferably less than 10 microns, and the coating is preferably 0.01 to 5 μm thick. The preferred porosity is provided by pores of the order of 0.05 to 0.01 microns. The coated membrane imparts high resistance to fouling by contact with whole blood, extends the linearity of the electrode response over a substantially greater range, e.g. in the analytical determination of glucose in blood, and combines a high degree of restriction to passage of interferents while retaining high permeability to hydrogen peroxide and oxygen. Most conveniently used for amperometric measurements, especially using a Clark electrode pair, with an "active" anode of platinum.

23 Claims, No Drawings

SENSOR DEVICES

This invention relates to sensor devices, and more particularly to improved sensor devices useful for analytical methods in enzyme-based electrode systems, and especially for use in biological systems.

It is known to make and use a variety of sensor devices which are based on a form of electrode in which the metal electrode is surrounded by membranes which can exclude interfering materials from the electrode surface while allowing substances to be determined by the analytical procedure to reach the electrode.

A common form is that in which the electrode assembly incorporates an enzyme, which acts on the substrate chemical being evaluated and generates a different chemical which can be determined, thus providing means for determining the substrate chemical indirectly. An especially useful form of this procedure uses glucose as the substrate and a glucose oxidase enzyme, so that these interact and—by catalyzed oxidation of the glucose to gluconic acid—produce hydrogen peroxide and oxygen as products. The hydrogen peroxide is very readily and conveniently determined electrolytically.

A problem encountered with such procedures is that the presence of other materials in the medium being analyzed can interfere with the operation of the sensor device (electrode). This can occur most markedly with high molecular weight materials, as in body fluids (e.g. by proteins and the like), but also can occur when one or more of the components of the electrolyte system is limited, in concentration or mobility, so that the signal output of the sensor (electrode) is in turn limited also. This effect has the most evident effect when it makes the output signal from the sensor (electrode) non-linear or reach a limiting value—as this restricts the range over which the sensor can be used effectively.

It has been proposed to use various materials as membranes, interposed between the electrode's active working surface and the medium under analysis, to prevent interfering materials reaching the electrode surface and fouling it, while still allowing the desired moieties to remain mobile and approach the electrode surface. Although this does produce useful results (controlled permeability and biocompatibility), the presence of any barrier tends to impose some limitations on mobility of the moieties present, and those barriers hitherto proposed have not yet proved to be entirely satisfactory.

We have now found that the properties of such barriers around the working surfaces of electrodes in sensor devices, usually termed "membranes," can be improved by application of a coating of a carbonaceous material to the material of the membrane. A carbonaceous material which we have found to be very effective is already well-known in itself and described in the art as "diamond-like carbon." It is conveniently referred to in the art by the abbreviation "DLC," and so is referred to in this manner through this specification.

DLC is a form of amorphous carbon or a hydrocarbon polymer with properties approaching those of diamond rather than those of other hydrocarbon polymers. Various names have been used for it, for example "diamond-like hydrocarbon" (DLHC) and "diamond-like carbon" (DLC), but the term "DLC" appears to be the most common. It possesses properties attributable to a tetrahedral molecular structure of the carbon atoms unit, similar to that of diamond but with some hydrogen atoms attached. It has been described in the art as being a designation for "dense amorphous hydrocarbon polymers with properties that differ markedly from those of other hydrocarbon polymers, but which in many respects resemble diamond" [J. C. Angus, EMRS Symposia Proc., 17, 179 (1987)].

Surprisingly, this "diamond-like carbon" coating, applied to a membrane, has an unexpectedly beneficial effect on the range over which the sensor can be used.

Thus according to our invention we provide an improved sensor device, useful in the electrolytic analysis procedures, which comprises a working electrode surrounded by at least one diffusion-limiting membrane, wherein the said membrane has a coating comprising a coating of a carbonaceous material having structural characteristics comparable with that of diamond.

Especially, we prefer to use a form of carbonaceous material known as "diamond-like carbon" ("DLC").

This has the advantage of allowing the electrolytic system to respond to the analyte being determined while extending the linear range over which the output signal of the sensor (i.e. from the working electrode) can be used.

The electrode itself may be any electrode having the properties of a working electrode, especially a metal electrode, and many are known in the art. It is preferably platinum metal, conveniently in any of the conventional forms for example as a 2 mm diameter platinum disc mounted in "Perspex" (poly-methyl methacrylate) surrounded by a silver ring of 2 cm diameter as a reference electrode. This is commonly referred to as the "Clark electrode assembly."

The membrane material may be any which is known in the art for the purpose of limiting access of undesired components, i.e. a permselective membrane material, but should be one which is of a nature which is compatible with the coating process (i.e. is durable enough to survive the coating treatment without itself being degraded or damaged appreciably) and which can retain the desired coating upon its surface. It is preferably a form of microporous membrane with low permeability, though other permselective materials may be used if desired, operative by their physical and/or chemical properties to give the desired porosity or permeability characteristics. In chemical terms, it is preferably a polycarbonate, as tis is a very durable material which accepts the coating well, but materials of other chemical constitution may be used if desired.

The membrane is preferably made of a thickness less than 10 microns. Such membranes are typically made by conventional methods, for example by rolling, cutting from a mass, casting from solution, or combinations of such techniques. The desired microporosity should be such as to provide pores in the membrane which are of the order of 0.05 to 0.01 microns in size. Such porosity may be achieved by known methods, for example by etching techniques—especially the technique known as "track etching" using a neutron beam. Such products are obtainable commercially under the name "Nuclepore" from Nuclepore, Pleasanton, Calif. or the Poretics Corporation (Livermore, U.S.A.). The polymer itself is impermeable to many higher molecular weight species while remaining permeable to low-molecular weight species such as hydrogen peroxide.

The formation and application of the diamond-like carbon (DLC) to the membrane material as coatings or films for the purposes of the present invention may be carried out by methods known in the art. It is usually formed by decomposition of carbon-containing compounds in gaseous or vaporized form (particularly hydrocarbon gases) induced by radiation or electrical fields.

Thus, it may be prepared from hydrocarbon precursor gases (e.g. propane, butane or acetylene) by glow-discharge deposition, by laser-induced chemical vapor decomposition, by a dual-ion beam technique, or by introduction of the hydrocarbon gases direction into a saddle-field source. A saddle-field source is a source of ions produced by a collision between gas atoms excited by thermionic emission, and this method is preferred because it allows heat-sensitive materials to be coated by a beam that is uncharged—so facilitating the coating of insulating or non-conductive materials.

Its properties can vary according to the particular raw materials used and its mode of formation. It can also be made in other ways, for example by sputtering solid carbon, as an alternative to dissociating hydrocarbon gases.

Further description of DLC—including its constitution, nature and properties, and the variations in its form which can be made—and modes for its preparation, are to be found for example in the following published references (among others):

(a) "Diamond-Like Carbon Applied to Bio-Engineering Materials;"0 A. C. Evans, J. Franks and P. J. Revell, of Ion Tech Ltd., 2 Park Street, Teddington, TW11 OLT, United Kingdom; Medical Device Technology, May 1991, pages 26 to 29.

(b) "Preparation and Properties of Diamond-like Carbon Films;" J. Franks; J. Vac. Sci. Technol. Vol. A, No. 3, May/June 1989, pages 2307–2310;

(c) "Biocompatibility of Diamond-like Carbon Coating;" L. A. Thompson, F. C. Law, J. Franks and N. Rushton; Biomaterials, Vol. 12, January 1991 (pages 37–40);

(d) "Categorization of Dense Hydrocarbon Films;" J. C. Angus; E.M.R.S. Symposium Proc., 1987, Vol. 17, page 179; Amorphous Hydrogenated Carbon Films, XVII, Jun. 2–5 1987, Edited by P. Koide & P. Oelhafen.

(e) "Properties of Ion Beam Produced Diamond-like Carbon Films;" M. J. Mirtech; E.M.R.S. Symposium Proc., 1987, Vol. 17, page 377;

(f) "Diamond-like Carbon—Properties and Applications;" J. Franks, K. Enke and A. Richardt; Metals & Materials (the Journal of the Institute of Metals); and (g) U.S. Pat. No. 4,490,229; M. J. Mirtich, J. S. Sorey & B. A. Banks.

Thus, in brief, our invention can be used as a method for providing a shield, useful for excluding interferents from an enzyme laminate/electrode assembly, comprising a coating of a carbonaceous material with properties approaching those of diamond as a covering material. The preferred carbonaceous material is that form of amorphous carbon or a hydrocarbon polymer known as "diamond-like carbon." Especially it is used as an outer covering material. It can also act as a biocompatible shield. The DLC may also be used to coat other parts of the electrode or sensor assembly if desired.

Alternatively stated, our invention provides improved sensor devices incorporating a coating of a carbonaceous material known as "diamond-like carbon" (DLC) as an outer shield, especially when bio-compatibility is desired. This coating allows the production of a shield with tailor-designed desirable diffusion characteristics.

The convenient source oft he carbon is a hydrocarbon gas or vapor, especially one which is readily decomposed by an electric field or discharge. A very convenient source gas is acetylene, though others may be used if desired. Individual hydrocarbons or mixtures thereof may be used, and diluent gases may be added if desired and the decomposition/ deposition procedure may be carried out at pressures at atmospheric or above or below atmospheric, as found most suitable for particular instances.

The coating may be made of a thickness which may be varied according to the particular requirements desired for the performance of the sensor and the system to be analysed. Thus, the thickness of the coating or deposit may be in the range 0.01 to 5 $\mu$m, but thicker or thinner coatings may be used if desired. A typical and convenient coating deposit is one approximately 0.1 $\mu$m thick, but this is not necessarily the optimum for all purposes. The thickness in any particular case will depend upon such factors as the nature (physical and chemical) of the material upon which the DLC is deposited, and its porosity or permeability, ad the particular characteristics appropriate to the intended use of the sensor.

The coating is conveniently carried out at a rate which allows the deposit to adhere to the membrane material and form a coating of the desired thickness—preferably also evenly coated so as to cover substantially all the surface without leaving any areas too thinly covered or even uncovered.

When using acetylene as a source, for example, the deposition may be carried out at a rate of up to 0.5 $\mu$m per hour, though higher or lower rates may be used if desired.

In carrying out the coating procedure, it is preferred that the membrane surface should be as clean as practicable, to ensure that the deposit has optimum ability to adhere properly. A variety of cleaning methods may be used. One which is very suitable is Fast Atom Bombardment (sometimes referred as "FAB" for brevity); this comprises subjecting the target material to a neutral atom beam source, and a typical cleaning time is an exposure to such treatment for about 5 minutes—though longer or shorter time may be used if desired.

If desired, more than one membrane may be used, and the coating may be applied to one or both surfaces of a membrane or to one or more surfaces of more than one membrane in the electrode assembly which makes up the sensor device.

Preferably, the coating is applied to the outer surface of the membrane (i.e. that surface remote from the active electrode and nearer to the surrounding media. If more than one membrane is used, the most advantageous position for the coating of DLC is on that membrane or membrane surface which is nearest to the medium being studied or analyzed.

Thus, for example, the sensor device may comprise an inner and an outer membrane, in which case one may be coated as defined above and the other may be either uncoated or may be of another material, coated or un-coated.

For example, the outer membrane may be as defined above and the inner may be for example made of a cellulose ester, and especially any form of cellulose acetate. Such a membrane is preferably made of a thickness in the range 0.1 to 1.0 $\mu$m, and may be made by conventional methods, for example by casting from solution, optionally with inclusion of additives (for example by inclusion in the casting solution) to modify the properties of the resulting cast film or to facilitate the casting process.

The invention is applicable to a variety of enzyme systems but is principally applicable to systems in which the enzyme is an oxidase and the hydrogen peroxide formed as a result of its action is measured electrolytically. Especially, it is useful for systems, sensors and electrodes incorporating a glucose oxidase enzyme, as the substrate glucose is a common component which requires to be measured for biochemical and clinical purposes. The use of the coated membranes in sensors according to the present invention enables the measurement or detection ranges for glucose to be extended considerably beyond those which are easily measurable by the sensors known hitherto, and also for the degree of linearity of response (i.e. the relationship between the sensor output signal and the amount of the substrate glucose) to be extended, which makes the sensors much more useful in practical clinical or laboratory conditions. Thus, as an illustration, ranges of glucose detection up to 25–30 mM of glucose are advantageous in practice and the present invention allows the range of detection to be extended even beyond this, for example to 100 mM or even more. Such high concentrations can be of value for measuring glucose concentration in media associated with products in the food and fermentation industries.

The enzyme may be incorporated in the sensor by conventional means, for example by being immobilized on the membrane by a fixing agent which does not impair its enzymic activity (for example glutaraldehyde and albumin), and a very convenient form of construction of the sensor is that in which the enzyme is held in place between two membranes—sometimes termed a "laminated" form of membrane. In such "laminates" one membrane layer (termed the outer layer) is the one exposed to the medium under study or analysis, and this is the one on which the diamond-like coating is of most value, though the coating can be on any or all membrane surfaces as desired.

The mode of electrolytic analysis to be used in especially amperometric analysis, which is well known and used in the art.

The principal advantage of our sensors is that they can be used in the reagent-less analysis of a wide variety of body fluids (e.g. blood or serum) and other biological media without dilution and without significant interference form endogenous or exogenous agents which may be present in a patient's blood. It enhances any membrane-based sensor system, Whether enzyme-based or not.

Diamond-like carbon coatings have the advantages of a high degree of inertness and also a high degree of haemocompatibility (compatibility with blood).

Further advantages of the present invention include:

(1) providing of a strong, flexible coating on the sensor;

(2) allowing the precise fine-tuning of the porosity to the outer membrane of a sensor, thus extending the linearity range;

(3) exclusion, by the coating, of large macromolecular and some smaller electrochemically active interferents, so preventing bio-fouling of the enzyme electrode assembly and enhancing the selectivity of the electrode, even to the extent that an outer membrane can provide the properties otherwise requiring the use of another, lower, underlying permselective membrane.

An especial advantage of the sensor of the present invention is that it will permit the reliable analysis of glucose concentrations in whole undiluted blood. This is usually not possible with the known forms of sensor. Of course, the value of the invention is not restricted to being solely applicable to the analysis of blood, and it may be applied to analysis of other media containing quite high concentrations of glucose or other electrochemically active species at levels which commonly present considerable problems for analysis. Such other media include a variety of a media of organic or non-organic origin, for example plant and fruit juices, chemical process liquids, and the like.

Thus according to our invention we also provide a method for the electrolytic analysis, especially of biological fluids, which comprises applying them to a sensor device or electrode system in which there is used a sensor electrode as defined above.

The preferred form of electrolytic analysis is amperometric detection.

Usually, the electrode of our invention will be used as the anode.

In use, the electrode of our invention can be used to carry out the method of our invention by immersion (together with an associated cathode) in a predetermined volume of a buffer solution to be analyzed, and applying a polarizing voltage so that the amperometric measurements can be made and compared before and after the addition of the blood or serum sample under test. The procedure may also be calibrated by use of solutions containing known amounts of the substances sought, and its accuracy this checked and confirmed. Likewise, the procedure may be carried out using known amounts of compounds which are considered to be potentially troublesome by their expected ability to interfere with the measurement of the paracetamol, so that the degree of interference (if any) can be established. Conventional apparatus may be used, for the cell, electrodes and the measurement and recording of the current-voltage relationships for the samples under test. Measurements may be made continuously or intermittently, as desired.

In operating the procedure, it is convenient to use a polarising voltage in the range +0.4 to 0.8 volts (preferably at approximately +6.5 volt) against a silver/silver chloride electrode. The liquid medium may be at a pH which can vary over a considerable range, but is especially in the pH range 6 to 8 and preferably at approximately 7.4 (for physiological use).

The sample under examination may be stirred or unstirred, as desired or convenient.

The electrolytic procedure for use of the sensors of our invention may be carried out over a considerable range of temperatures, for example in the range 20 to 40 degrees C.. It is usually important that the temperature used for calibration is within approximately 4 degrees C. of the assay temperature.

For calibration, an isotonic or other other buffer may be used, but it is preferable to use one which has an ionic strength similar to blood (i.e. approximately 0.15M).

The medium is commonly aqueous, but need not necessarily be so, and an organic solvent may be used if desired (as such, or in admixture with each other and/or water) provided it is an electrolyte and dissolves any desired reagents, but is not medically relevant to the assay carried out.

Typically, a procedure for calibration uses a treatment in isotonic phosphate buffer at pH 7.4. Following this, the buffer is removed, the serum or blood is added, and the response is awaited; this illustrates how much the procedure can become a simplified analysis.

For this purpose, the electrode may be immersed in a sample of the fluid (e.g. blood) and then linked with a suitable reference electrode (for example a silver electrode or a calomel electrode) in conventional manner. Measurement of the voltage, current and the like may be taken and the measurements taken and recorded as desired, intermittently or continuously. For this, conventional apparatus may be used.

Samples of the media for examination (for example blood or serum) may be obtained by standard methods. The quantity of blood/serum should be sufficient to cover the electrode and the current measured at a fixed time or after a stable response has been achieved. Likewise, samples of other media may be obtained in any convenient manner and brought into contact with the sensor of the present invention for the purpose of component detection.

The membrane and/or anode may be prepared for use in the analytical process of the invention by soaking it, when it is in place around the anode, in a solution corresponding to the electrolyte medium before the blood/serum sample is added.

Similar procedures and conditions may be used for analysis of other media of a biological or biochemical nature, with modifications as will appear appropriate to an expert in the art having regard for the nature of the media, the components sought, and the conditions and requirements of the measurement.

The invention is illustrated, but not limited, by the following Examples.

EXAMPLES

Chemicals

Glucose oxidase from *Apergillus niger* (75% protein, 150,000 units/g solid), and bovine serum albumin (fraction V), were obtained from the Sigma Chemical Company Limited (Poole, Dorset), D-glucose, di-sodium hydrogen phosphate, di-hydrogen sodium phosphate, sodium benzoate and sodium chloride ("AnalaR" grade) were obtained from BDH (Poole, Dorset). All chemicals were used without further preparation.

Buffer

A buffer (pH 7.4) of $5.28 \times 10^{-2}$M $Na_2HPO_4$, $1.3 \times 10^{-2}$M $NaH_2PO_4$, $5.1 \times 10^{-3}$M sodium chloride, $6.24 \times 10^{-3}$M sodium benzoate was prepared in distilled water. This buffer was used for all enzyme preparations and diffusional studies.

DLC Coated Polycarbonate Membranes

Polycarbonate membranes for DLC coating were purchased from Poretics Corporation (Livermore, USA) and the DLC coating procedure performed by Atom Tech Ltd. (Teddington, Middlesex, England—formerly Ion Tech Limited) as has been described (J. Franks; J. Vac. Sci. A71 (1989), page 2307). Polycarbonate membranes of pore radii 0.01, 0.05 and 0.1 µm were prepared with deposition durations of DLC of 1 minute, 3 minutes 30 seconds, and 7 minutes and compared with un-coated membranes. Membranes were cleaned by a 5 minute Fast Atom Bombardment (FAD) within an argon or other gaseous saddle field source. Control membranes were similarly treated.

DLC coating times quoted define deposition times, so single-sided coated membranes had all of the deposition of DLC applied to one surface, while double-sided coated membranes had 50% applied to each surface. In this way it was intended that single and double sided coated membranes could be directly compared with regard to coating durations. The deposition rate of DLC was 0.45 µm per hour, so 1 minute, 3 minutes 30 seconds, and 7 minutes coating correspond to 0.0075, 0.0225 and 0.05 µm thickness respectively. These membranes had a quoted thickness of 6 µm, so the maximum coating of DLC was less than 1% of the membrane thickness to which it was applied. It was therefore assumed to have a negligible effect on the thickness of the membranes used in the calculation of the P values.

Apparatus

An oxygen electrode assembly (Range Brothers, Bottisham, Cambridge, U.K.) as previously used (W. H. Mullen, S. J. Churchouse, F. H. Keady and P. M Vadgama; Anal. Chim, Acta. 183 (1986), page 59) was utilised for glucose oxidase enzyme electrodes. The working electrode (anode) was polarized at +650 mv (vs Ag/AgCl) for the oxidation of hydrogen peroxide. The cell was comprised of a central 2 mm diameter platinum disc with an outer pre-anodized 12 mm diameter 1 mm silver ring (Ag/AgCl) as a combined reference and counter electrode. The purpose-built voltage polarisation source and potentiostat were constructed by the Chemistry workshops (University of Newcastle, U.K.), and a x-t chart recorder (Lloyd Instruments plc, Fareham, Hants., U.K.) was used to record amperometric responses of the electrode assembly from the potentiostat current follower. A blood gas analyzer (Instrumentation Lab Model IL 1802- Hope Hospital, Clinical Biochemistry Laboratory) was used for the analysis of $pO_2$ within buffer aliquots.

Fabrication of Enzyme Electrodes

Glucose oxidase (GOD) (2560 units/ml) and bovine serum albumin (BSA) (0.1 g/ml) were dissolved in buffer solution. 6 µl of GOD/BSA solution and 3 µl of glutaraldehyde (5% v/v) were mixed rapidly and placed on a 1 $cm^2$ portion of 0.05 µm polycarbonate membrane. A 1 $cm^2$ portion of DLC-coated polycarbonate membrane was then placed on top and glass slides were used to compress the enzyme and membrane laminate under finger pressure for approximately 5 minutes. The resulting cross-linked enzyme laminate was placed over the working electrode, prior to final electrode assembly and fixation by an "O" ring.

Methodology: Determination of Permeability Coefficients

Solute mass transfer measurements across DLC-coated polycarbonate membranes to assess their permeability were performed at 22±1 degrees C. in a Classical diffusion chamber apparatus consisting of two chambers. Both chambers were of 170 ml volume and were separated by two stainless steel discs and two sealing rubber "O" rings clamped together to hold the membrane of interest with a cross-sectional area available for mass transport of 7.07$cm^2$. The solute of interest was added to one chamber and mass transfer was then determined by measuring solute concentrations in both chambers at periodic intervals. For the determination of $pO_2$ levels, aliquots were extracted by a syringe and sealed within small glass vessels to prevent mixing with the atmosphere, prior to $pO_2$ analysis. Oxygen within one chamber was consumed by placing cross-linked GOD/BSA films in excess, to create oxygen gradients across the membrane of interest. $pO_2$ levels were determined by the blood gas analyser. Permeability coefficients were calculated using the expression derived by Sun et al. (Biotech. Bioeng., 34, (1989), page 55).

Analysis of Blood Glucose Concentrations

Blood samples previously tested for glucose concentrations (Hope Hospital Clinical Biochemistry laboratory) were used for the assessment of enzyme electrodes for whole blood analysis. Blood samples were used on the same day as the hospital analysis and stored under refrigeration in tubes containing fluoride oxalate prior to use to prevent the lowering of blood glucose levels with time due to cell metabolism.

Results

Polycarbonate membranes (Poretics Corporation) incorporate near cylindrical channels, formed by a well established neutron beam track-etched method. The relatively low thickness (approx. 11 µm) of these membranes has enabled minimization of diffusional distances, while facilitating a high degree of control over diffusional resistance. The glucose/$O_2$ permeability coefficient, P, ratio is of critical significance if the membrane is to be used as a substrate diffusion limiting outer membrane over oxidase enzymes. By minimizing the glucose/$O_2$ P ratio for membranes, enzyme electrodes were constructed that became diffusion controlled rather than reflecting intrinsic enzyme kinetics.

DLC-coated polycarbonate membranes have now allowed further extension of linearity for glucose analysis within in vitro samples (>80 mM), and also enabled minimization of bio-fouling to the sensor. A series of experiments was performed to determine the P values for $O_2$ and glucose across a spectrum of DLC single and double sided coated membranes, using a diffusion chamber apparatus (A. C. Evans, J. Franks and P. J. Revell; Medical Device Technol., 26 (1991) page 26). On each occasion three membranes of each type were independently tested within the diffusion chamber, and a mean value for each P value calculated. To aid clarity, only this value is used in describing permeability coefficients trends.

We studied how the P values for glucose and $O_2$ are related to polycarbonate membranes of 0.01, 0.05 and 0.1 μm pore radii, with different durations of single and double sided DLC coating. This demonstrated that, typically, P values across three membranes prepared by the same procedure may be attained to within a margin of around 5%. The production of membranes, the coating procedure and methodology for the evaluation of P values is therefore shown to be reproducible.

We found that the P values for both glucose and $O_2$ decrease with decreasing pore radius and with increasing DLC coating time, which is consistent with the finding that as the pore area is encroached, the diffusional resistance to solute trans-membrane transport increases. In particular, we found that P values for glucose progressively diminish as the DLC coating thickness is increased, due to the pore area being progressively diminished. No previous technique used by us (e.g. organic solvent deposition) has allowed such "fine tuning" of membrane permeability at small pore radii. Our results indicated that, for a similar application of DLC, whether it is to a single surface or to both membrane surfaces has little influence on the diffusion species' behaviour across the membrane.

0.01 μm pore radii polycarbonate membranes were found to be blocked to glucose transport when greater than 1 minute duration coatings of DLC are applied. However, single sided coated membranes become blocked at >1 minute DLC coating durations, whereas diffusion of glucose is permitted for double sided coated membranes of 1 minute DLC coating duration. This blocking difference is believed to be due to the build-up of DLC at very small pores in single sided coatings, whereas the pore aperture is spared if this is distributed across two membrane surfaces. Of particular interest, however, is the finding that $O_2$ transport is much less affected by DLC application, ad that when glucose is fully obstructed $O_2$ trans-membrane transport is still maintained. The P ratio values are very similar for single or double sided DLC-coated membranes. The first application of DLC (1 minute) results in the greatest reduction of the glucose/$O_2$ P ratios. Further coatings of DLC result in continued reduction in this ratio, although the effect is less prominent. The membranes showing the smallest glucose/$O_2$ P ratios are those for 0.05 μm pore radii membranes with 7 minutes DLC coating, for both single and double sided coated membranes.

We carried out the calibration of glucose oxidase enzyme electrodes with upper double sided 0.01 μm pore radii membranes and the corresponding control. Linear ranges of analysis were found to be possible to in excess of 80 mM concentrations, which are vastly in excess of those that may be attained with un-coated membranes.

Further work was carried out on calibration curves for enzyme electrodes employing upper 0.05 μm pore radii membranes. The almost identical behaviour shown by enzyme electrodes utilizing single and double sided DLC-coated membranes confirms that, for both types of membrane, the same coating times impart almost identical properties. In addition, as the DLC coating time is increased, the enzyme electrode linearity range is progressively extended.

Similar findings are shown for 0.1 μm pore radii upper membrane enzyme electrodes and the calibration curves for sensors utilizing 0.1 μm pore radii DLC-coated upper polycarbonate membranes. Again, longer durations of DLC coating result in extended linearity ranges.

A major constraint to the commercialization of previously known sensors for whole blood measurements has been the intractable problem of signal drift as a result of bio-fouling.

A series of experiments was designed so that the enzyme electrodes, all with inner 0.05 μm pore radii un-coated polycarbonate membranes, and varying pore radii DLC-coated outer polycarbonate membranes (together with controls) were exposed to heparinized whole blood and then rinsed with non-anticoagulated buffer solution. Responses to 5 mM glucose solutions, before and after blood exposure, were recorded and percentage losses of response were calculated.

The percentage losses of signal following exposure to whole blood for 30 minutes was calculated. Results showed a typical loss of response to a standard 5 mM buffered glucose solution, following increasing time exposure to whole blood. Again, very few differences were observed between single or double sided DLC-coated membranes. However, the resistance to bio-fouling appears to increase with greater deposition of DLC for all membranes.

The greatest change is seen between un-coated membranes and the first deposition of DLC (1minute). The polycarbonate membrane pore radius also appears to be critical, as smaller pore radii membranes always exhibit lower losses following blood exposure than enzyme electrodes with similar DLC-coated membranes of larger pore radii. It therefore appears that both smaller pore radii and longer durations of DLC coating contribute to increased functional bio-compatibility.

As before, only double sided DLC-coated membranes of 0.01 μm pore radii could be tested for bio-fouling as single sided DLC-coated 0.01 μm pore radii membranes were all blocked to glucose. However, 0.01 μm pore radii polycarbonate membranes with 1 minute deposition DLC double-sided coatings as the upper membrane of an enzyme laminate exhibited extreme resistance to bio-fouling, showing a low of only 6% signal following 30 minutes exposure to whole blood. This is considerably better than has been achieved to date with other membrane systems to our knowledge.

An enzyme laminate with an upper nominal pore radius of 0.1 μm and 7 minutes double-sided DLC coating was exposed to blood, washed with distilled water, and buffer placed in the cell for continued washing for one hour. The buffer was then replaced with a 5 mM glucose buffer and the response recorded. The final response was found to be 4% higher than previously noted, believed to be because some surface bio-fouling had been mechanically dislodged.

As linearity ranges for glucose analysis over clinically useful ranges had been attained, and the effects of bio-fouling assessed following whole blood exposure, two sensors for comparison were constructed—both with lower 0.05 μm pore radii polycarbonate membranes; outer membranes were of 0.01 and 0.1 μm pore radii double sided 1 minute duration DLC-coated membranes. These two enzyme electrodes were calibrated following exposure to whole blood, and individual blood samples previously tested for glucose levels within a Clinical Biochemistry Laboratory (at Hope Hospital) were analyzed and the correlations between the two electrodes and the Clinical Laboratory results were studied. The 0.01 μm pore radii upper membrane glucose electrode yielded results which were in close agreement with those of the Biochemistry Laboratory, though the results for 0.1 μm pore radii membranes showed a poorer correlation. This has two important consequences. The correlations show that this enzyme electrode is capable of yielding consistently reliable results for the analysis of blood glucose concentrations despite repeated exposure to whole blood. Secondly, although no permselective membrane has been used, the electrode appears to show little sign of electroactive interferents reaching the working electrode, indicating that the upper membrane is uniquely acting as a barrier to electroactive interferents.

Conclusions

A comprehensive series of DLC-coated microporous polycarbonate membranes have been assessed in terms of porosity and permeability coefficients calculated for glucose and oxygen using the classical diffusion chamber.

Glucose electrodes have been constructed utilizing DLC-coated outer covering membranes, and linearity ranges assessed for sensors possessing a series of DLC-coated membranes. Comparisons have been made between the permeability coefficient of glucose and oxygen, and P ratios related to linearity ranges attained using these membranes. Lower glucose/$O_2$ ratios were found to be associated with extended linearity ranges. Linearity ranges in excess of 80 mM glucose concentrations were attained using 0.01 μm, 1 minute duration DLC-coated, polycarbonate membranes as outer covering membranes. The enzyme electrode utilized the membrane showing the greatest diffusional resistance to glucose, suggesting that the glucose/$O_2$ P ratio and the absolute P value for glucose are both critical for linearizing a glucose enzyme electrode. The same enzyme electrode exhibited a good resistance to bio-fouling, with losses in response of only 6% following repeated exposure to whole blood as well as showing close correlation to glucose analysis using conventional Clinical Biochemistry techniques, despite the absence of an underlying selective membrane.

We claim:

1. A sensor device, useful for electrolytic analytical procedures, incorporating a carbonaceous material having characteristics comparable with that of diamond known as diamond-like carbon which serves as a shield to exclude interferents.

2. A sensor device as claimed in claim 1 in which a working electrode is surrounded by at least one diffusion-limiting membrane, wherein the said membrane has a coating comprising a carbonaceous material having characteristics comparable with that of diamond known as diamond-like carbon.

3. A sensor device as claimed in claim 1 or claim 2 wherein the working electrode is a metal.

4. A sensor device as claimed in claim 3 wherein the metal is platinum.

5. A sensor device as claimed in claim 4 wherein the working electrode is in the form of a platinum disc surrounded by a silver ring as reference electrode.

6. A sensor device as claimed in claim 1 or claim 2 wherein the membrane is made of a permselective membrane material comprising a microporous membrane with low permeability.

7. A sensor device as claimed in claim 6 wherein the membrane has pores which are of the order of 0.05 to 0.01 microns in size.

8. A sensor device according to claim 6 wherein the microporous membrane is a polycarbonate.

9. A sensor device as claimed in claim 2 wherein the membrane has a thickness less than 10 microns.

10. A sensor device as claimed in claim 2 wherein the coating of diamond-like carbon is of a thickness in the range 0.01 to 5 μm.

11. A sensor device as claimed in claim 2 wherein the membrane is cleaned before coating.

12. As sensor device as claimed in claim 2 wherein the coating of "diamond-like carbon" is applied to the outer surface of the membrane or, if more than one membrane is used, the coating of diamond-like carbon is on that membrane or membrane surface which is nearest to the medium being studied or analyzed.

13. A sensor device according to claim 12 wherein the diamond-like carbon is applied to the surface remote from the active electrode and nearer to the surrounding media.

14. A sensor device as claimed in claim 1 or claim 2 wherein the sensor contains an enzyme system and the hydrogen peroxide formed as a result of its action is measured electrolytically.

15. A sensor device as claimed in claim 14 wherein the enzyme is held in place between two membranes.

16. A sensor according to claim 14 wherein the enzyme system comprises an oxidase.

17. A method for electrolytic analysis which comprises applying a fluid to be anlayzed to a sensor device or an electrode system comprising a sensor electrode as defined in claim 1 or claim 2.

18. A method for electrolytic analysis as claimed in claim 17 wherein the electrolytic analysis is amperometric detection.

19. A method for electrolytic analysis as claimed in claim 17 applied to the reagent-less analysis of a body fluid.

20. A method according to claim 19 wherein the body fluid is blood.

21. A method for electrolytic analysis as claimed in claim 17 wherein there is used a polarizing voltage in the range +0.4 to 0.8 volts against a silver/silver chloride electrode.

22. A method for electrolytic analysis as claimed in claim 17 wherein the sensor is calibrated at a temperature within approximately 4 degrees C. of the assay temperature.

23. A method for electrolytic analysis as claimed in claim 17 wherein the sensor is first treated with a buffer solution.

* * * * *